United States Patent [19]
Hosoi et al.

[11] Patent Number: 5,260,029
[45] Date of Patent: Nov. 9, 1993

[54] FLUORESCENCE DETECTION OF DNA BASES

[75] Inventors: Shigeru Hosoi; Tsuyoshi Hayakawa, both of Hamamatsu, Japan

[73] Assignee: Hamamatsu Photonics K.K., Shizuoka, Japan

[21] Appl. No.: 917,384

[22] Filed: Jul. 23, 1992

[30] Foreign Application Priority Data

Jul. 23, 1991 [JP] Japan .................. 3-182478

[51] Int. Cl.⁵ .......................................... G01N 21/64
[52] U.S. Cl. ................... 422/82.08; 422/82.05; 250/458.1; 250/461.2; 356/317; 356/318
[58] Field of Search ................. 422/82.05, 82.08; 356/317, 318; 250/458.1, 461.2, 207

[56] References Cited

U.S. PATENT DOCUMENTS

| | | | |
|---|---|---|---|
| 3,849,654 | 11/1974 | Malvin | 356/317 X |
| 4,115,699 | 9/1978 | Mizuta et al. | 250/461.2 |
| 4,352,558 | 10/1982 | Eisert | 250/461.2 X |
| 4,600,302 | 7/1986 | Sage, Jr. | 356/317 X |
| 4,643,566 | 2/1987 | Ohe et al. | 356/317 X |
| 4,778,593 | 10/1988 | Yamashita et al. | 250/461.2 X |
| 4,825,066 | 4/1989 | Nakamura et al. | 250/207 |
| 4,855,930 | 8/1989 | Chao et al. | 356/318 X |

Primary Examiner—James C. Housel
Assistant Examiner—Maureen M. Wallenhorst
Attorney, Agent, or Firm—Sughrue, Mion, Zinn, Macpeak & Seas

[57] ABSTRACT

To assure detection of fluorescence produced from continuously supplied fine particles such as DNA bases with accuracy and excellent efficiency, fine particles supplied from a flow cell are introduced into a through-hole of a hollow photomultiplier. An optical fiber is disposed in axial alignment with the through-hole of the photomultiplier and irradiates an exciting light beam onto the fine particles staying in the through-hole. Light-induced fluorescence is thus detected by the photomultiplier which has a photocathode on an inner circumference of the through-hole.

10 Claims, 7 Drawing Sheets

FIG. 7A
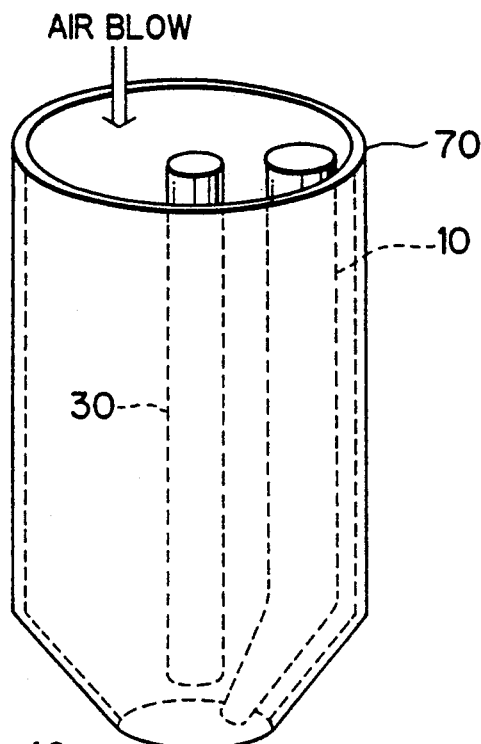
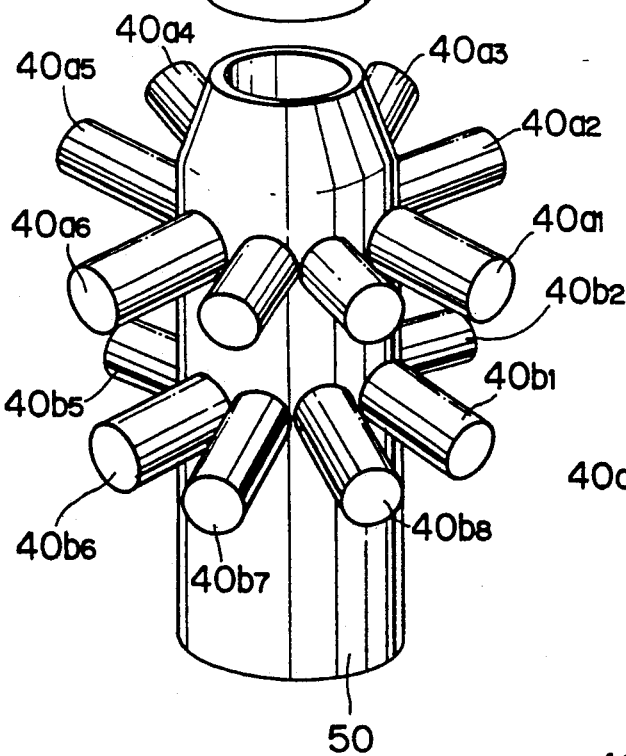
FIG. 7B
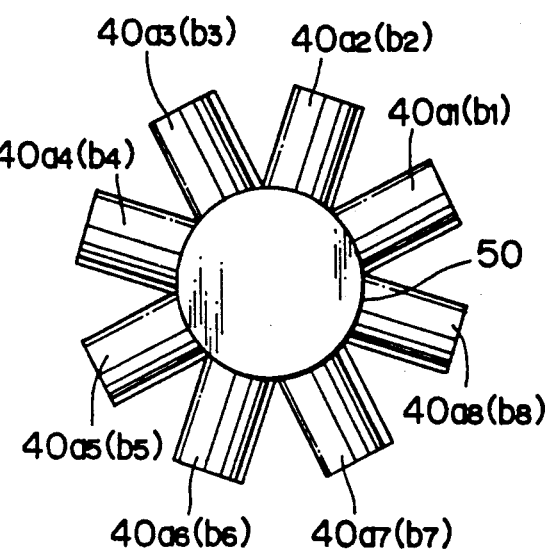

FLUORESCENCE DETECTION OF DNA BASES

BACKGROUND OF THE INVENTION

1. Field of the Invention

The present invention relates to a fluorescence detection of a fine particle, and more particularly to a fluorescence detection of a base (nucleotide) forming a gene.

2. Description of the Prior Art

Deoxyribonucleic acid abbreviated to DNA is composed of bases as a primary component, sugar and phosphoric acid, and is in a double helix structure containing genetic information therein. The genetic information is present in each of the DNA fragments in the form of a sequence of bases. A strand of genes is found in the cell of an organism. For lower animals such as a microorganism, there are several thousand base pairs while for a higher level animal having much more genetic information, there are several hundred million to nearly three billion base pairs.

The genetic information of DNA is determined by a sequence of adenine (A), guanine (G), cytosine (C), and thymine (T) which are bases (nucleotides) forming a nucleic acid. Investigation of the sequence of these bases is therefore the key to develop gene engineering and medical science.

It has been known that each of the aforesaid bases produces specific fluorescence, and it has been practiced to identify the base depending upon the fluorescence produced. Production of fluorescence results from irradiation of exciting light onto the base. Detection of the fluorescence thus produced may preferably be performed using a high sensitivity detector such as photomultiplier tube.

A publication entitled "Chemical Physics Letters" (1990) 174, pages 552-557 discloses an arrangement for detecting fluorescence as shown in FIG. 1. An exciting light from a light source 62 is irradiated into a flow cell 61 wherein the direction C in which the exciting light is irradiated is perpendicular to the direction $A_1$ in which fine particles are supplied to the flow cell 61. The fluorescence emitting in the direction of D is detected by a photomultiplier tube 63, wherein the direction D is perpendicular to both the direction $A_1$ and the excited light irradiation direction C.

The arrangement as above is, however, incapable of accurately and efficiently detecting the fluorescence from the fine particle such as the base of gene. A single DNA fragment has an extremely large number of bases, and thus each base is extremely small in size, and the fluorescence produced from each base is extremely minute. It is therefore difficult to identify the kind of the base with the detection of the fluorescence which takes place for an ultra short period of time when the exciting light beam passes through the fine particle.

While it it is possible to prolong a period of time during which the fluorescence is produced and enhance the efficiency of fluorescence detection if the exciting light beam is irradiated over the streamwise range of the fine particles, a problem arises that processing of the data collected is difficult because sequentially supplied fine particles are detected one at a time. The conventional arrangement has a further disadvantage that only the fluorescence produced in one direction can be detected, and thus it is low in efficiency.

SUMMARY OF THE INVENTION

In view of the foregoing, it is an object of the present invention to provide an arrangement which assures accurate and efficient detection of fluorescence produced from continuously supplied fine particles.

To achieve the above and other objects, there is provided a device for detecting fluorescence produced from a fine particle, comprising supplying means for supplying fine particles in a direction, blowing means for blowing the fine particles to move in a direction at a speed higher than a speed at which the fine particles are supplied from the supplying means, and irradiating means for irradiating an exciting light beam onto the fine particle. The irradiating means has an optical axis in alignment with the direction in which the fine particles are moved by the blowing means. There is provided detecting means for detecting fluorescence produced from the fine particle which is excited by the exciting light while being moved by the blowing means.

In preferred embodiments of the present invention, the direction in which the fine particles are moved by the blowing means may either be substantially orthogonal or substantially parallel to the direction in which the fine particles are supplied by the supplying means.

The detecting means is formed with a through-hole through which the exciting light and the fine particles being moved by the blowing means pass.

In accordance with the present invention, the fine particle supplied from the supplying means is introduced into the through-hole of the detecting means by the blowing means, and the fine particle is kept irradiated while it stays in the through-hole. Therefore, the fluorescence producing time is prolonged and the fluorescence thus produced can be captured by the light detecting surface provided in the inner circumference of the through-hole.

BRIEF DESCRIPTION OF THE DRAWINGS

The particular features and advantages of the invention as well as other objects will become apparent from the following description taken in connection with the accompanying drawings, in which:

FIGS. 7A and 7B are vertical cross-sectional and top plan views, respectively, showing another embodiment of the present invention.

DETAILED DESCRIPTION OF THE PREFERRED EMBODIMENTS

Figure 1:
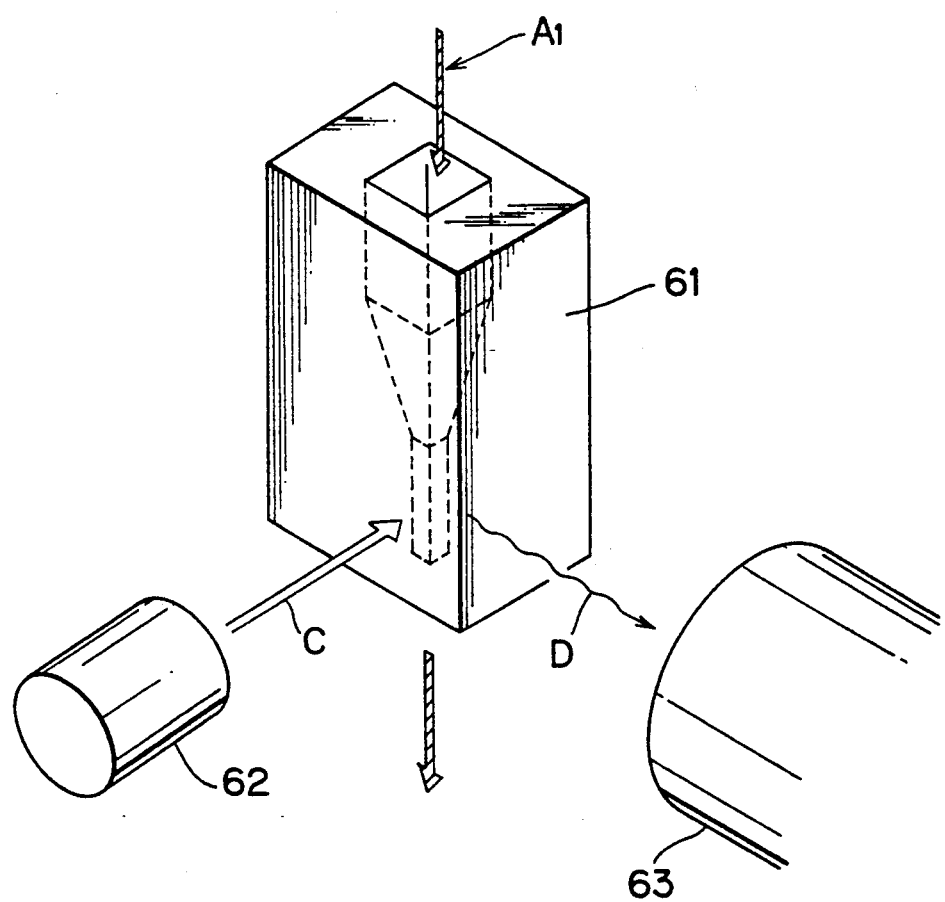
FIG. 1 is a perspective view showing a conventional arrangement for detecting fluorescence of fine particles.
Figure 2:
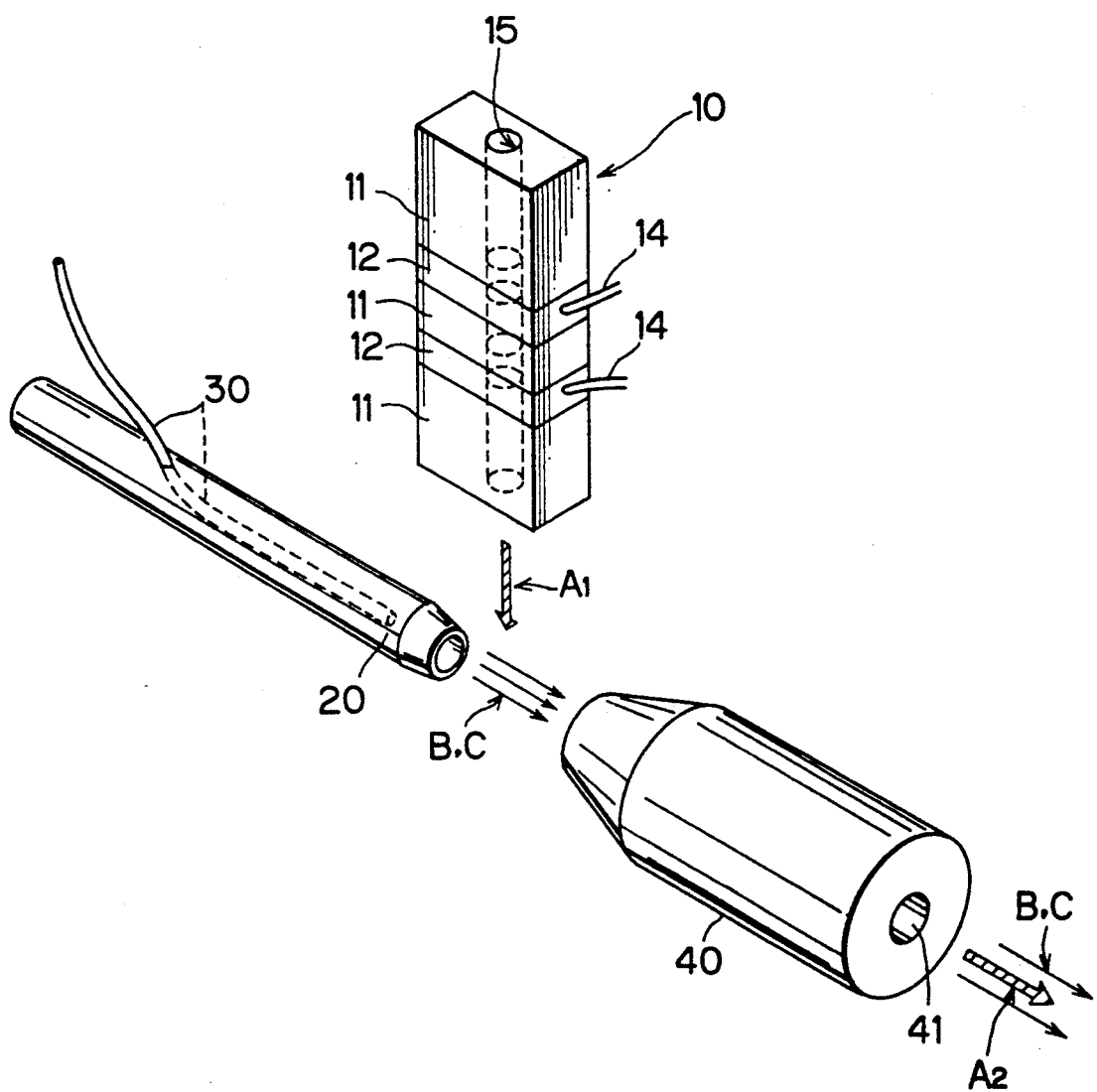
FIG. 2 is a perspective view showing an arrangement for detecting fluorescence of fine particles according to an embodiment of the present invention.

A fine particle fluorescence detection device according to a preferred embodiment of the present invention is shown in FIG. 2. The device includes a single molecular, continuously trapable flow cell 10, a flow booster 20 which produces gas jet for blowing fine particles, a light guide member 30 arranged to emit an exciting light coaxially of the flow booster 20, and a hollow photomultiplier 40 which has an axially extending through-hole 41 and is arranged so that the through-hole 41 is in coaxial relation to the flow booster 20. The hollow photomultiplier 40 serves as a photodetector. The fine particle dropping direction $A_1$ from the flow cell 10 is orthogonal to both the gas jetting direction B from the flow booster 20 and the direction C of an optical axis of the exciting light. A light source (not shown) is connected to the light guide member 30.

Figure 3:
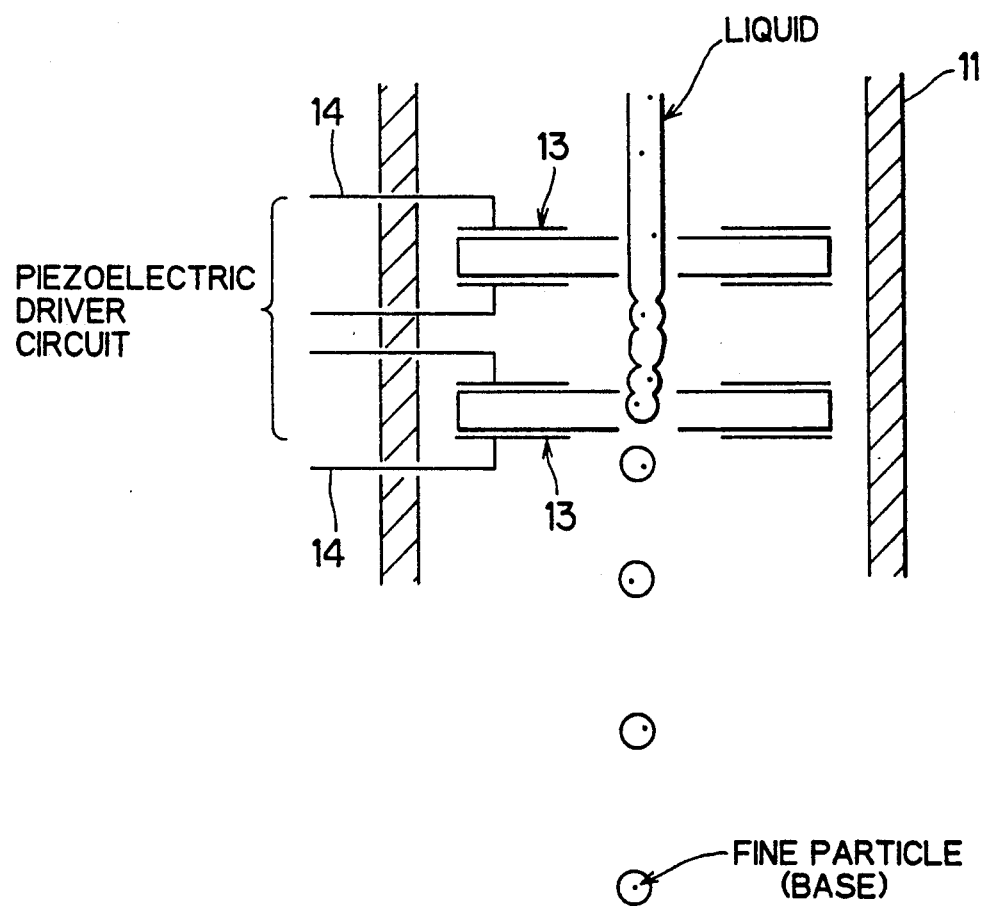
FIG. 3 is an explanatory diagram for description of an essential portion of a flow cell used in the embodiment of the present invention.

The flow cell 10 has two supersonic traps 12 sandwiched between three-divided flow cell blocks 11. As shown in FIG. 3, each supersonic trap 12 has a piezoelectric element 13 which is connected to a piezoelectric driver circuit through wires 14. The flow cell 10 has a flow path through which fine particles dispersed in liquid are allowed to flow. The piezoelectric elements 13 form a standing wave in the interior of the flow path, whereby the liquid droplets are produced and fall through the flow cell 10.

Figure 4:
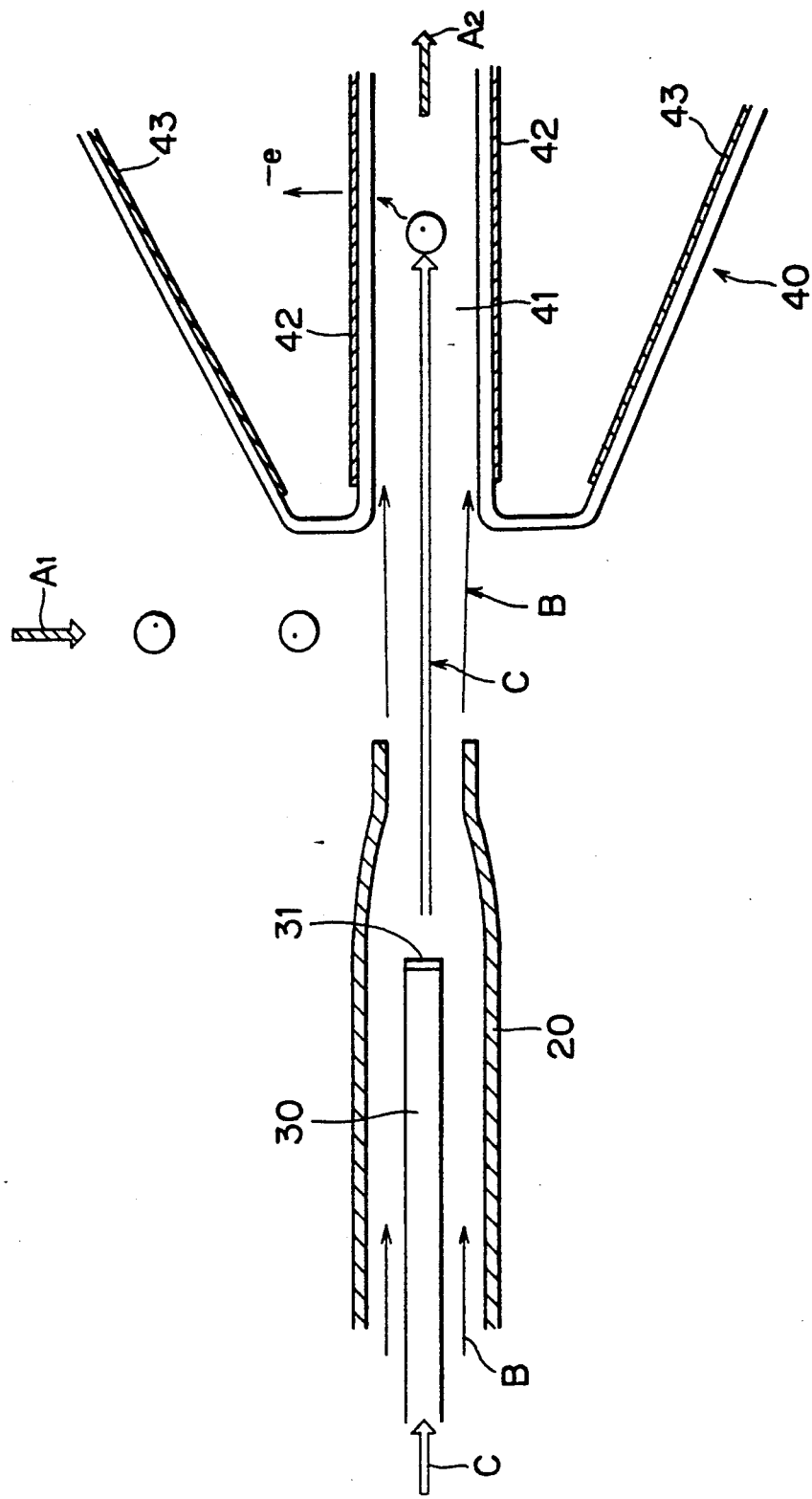
FIG. 4 is a cross-sectional view showing a relationship between a flow booster, light guide and a hollow photomultiplier tube.

FIG. 4 illustrates a state in which the fine particle droplets are dropped from the flow cell 10. The flow booster 20, the light guide member 30 and the hollow photomultiplier 40 are arranged in axial alignment with one another in a direction orthogonal to the fine particle dropping direction $A_1$. The light guide member 30 is coaxially disposed within the flow booster 20. A photocathode 42 is provided over the entire inner circumference of the through-hole of the hollow multiplier 40. A first dynode 43 is provided in substantially confrontation with the photocathode 42. The dropped fine particle droplets are directed toward the inner space of the through-hole 41 of the hollow multiplier 40 due to gas jets produced from the flow booster 20. The fine particle is moved in the direction of $A_2$ which is the same direction as the gas ejection direction B but at a higher speed than the dropping speed. At this time, the fine particle is kept irradiated by the exciting light emitted from the end surface 31 of the light guide member 30, thus producing fluorescence. Since the production of the fluorescence occurs in the internal space of the photomultiplier 40, the major part of the fluorescence is incident on the photocathode 42 to thus produce photoelectrons. Therefore, the fluorescence detection can be performed with high efficiency.

Figure 5:
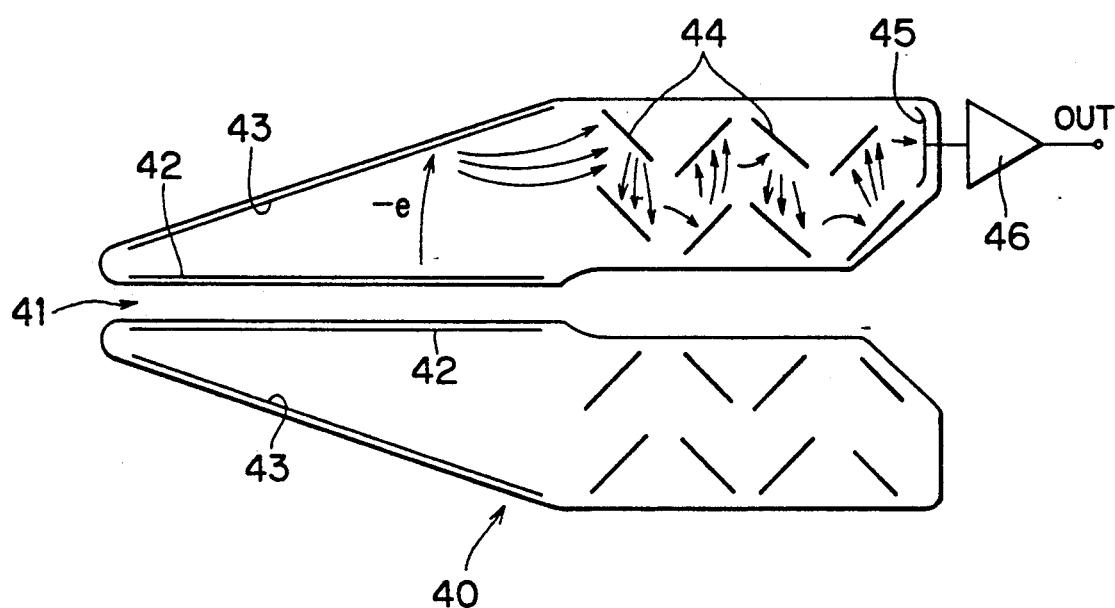
FIG. 5 is a cross-sectional view showing the hollow photomultiplier tube used in the embodiment of the present invention.

FIG. 5 shows an internal arrangement of the hollow photomultiplier 40. As shown, the photocathode 42 is provided on the entire inner circumference of a smaller-diameter portion of the through-hole 41. The first dynode 43 is provided in substantially confrontation with the photocathode 42 and the second dynode 44 is provided to receive the secondary electrons emitted from the first dynode 43. Similarly, appropriate number of stages of the dynodes are arranged in succession in the axial direction of the photomultiplier 40. An anode 45 is provided to receive the electrons emitted from the final stage dynode. The output of the anode 45 is amplified by an amplifier 46 and derived from an output terminal (OUT). In this manner, the photoelectrons produced depending on the fluorescence of the fine particle are successively multiplied by a number of dynodes 43, 44 and are taken out from the output terminal (OUT).

According to the above-described embodiment, the direction $A_2$ in which the fine particle advances is in coincidence with the optical axial direction C of the exciting light, so that the fine particles can be excited by the converged exciting light beam over a long period of time. Further, detection of the fluorescence can be attained with high efficiency, since the fluorescence emanating from the fine particles is produced in the interior of the through-hole 41 of the hollow photomultiplier 40 and thus the fluorescence is almost perfectly incident on the photocathode 42. As such, extremely minute fluorescence emanating from a fine particle such as a base forming a gene can be detected.

Another embodiment of the present invention will be described with reference to FIGS. 7A and 7B. In this embodiment, the fine particle supplying direction and the optical axis of the exciting light are set substantially in parallel to each other. More specifically, a single molecular, continuous trappable flow cell 10 and an optical fiber or light guide member 30 are disposed interiorly of a cylindrical member 70 to be in parallel to each other. To introduce the fine particles supplied from the flow cell 10 into a photo-detecting cylinder 50 at a higher speed, air is blown into the inner space of the cylindrical member 70. Two sets of photodetectors $40a_1$ through $40a_8$ and $40b_1$ through $40b_8$ are provided on the outer circumference of the photo-detecting cylinder 50. The photodetectors $40a_1$ through $40a_8$ or $40b_1$ through $40b_8$ are arranged equi-angularly. It is preferable that the number of the photodetectors in each set be 6 or 8.

While the present invention has been described with respect to a specific embodiment, it can be appreciated to those skilled in the art that a variety of changes and modifications can be made without departing from the scope of the invention. For example, bubble jet nozzles used in bubble jet printers may be used in place of the ultrasonic traps for use in a single molecular, continuously trappable flow cell. Two or three hollow photomultipliers 40 may be coupled together in series to provide two- or three-stage hollow multipliers with which the detection efficiency can be further improved. Provision of a wavelength filter in the opening of the through-hole 41 can prevent detection of noises caused by scattering of the exciting light.

Figure 6:
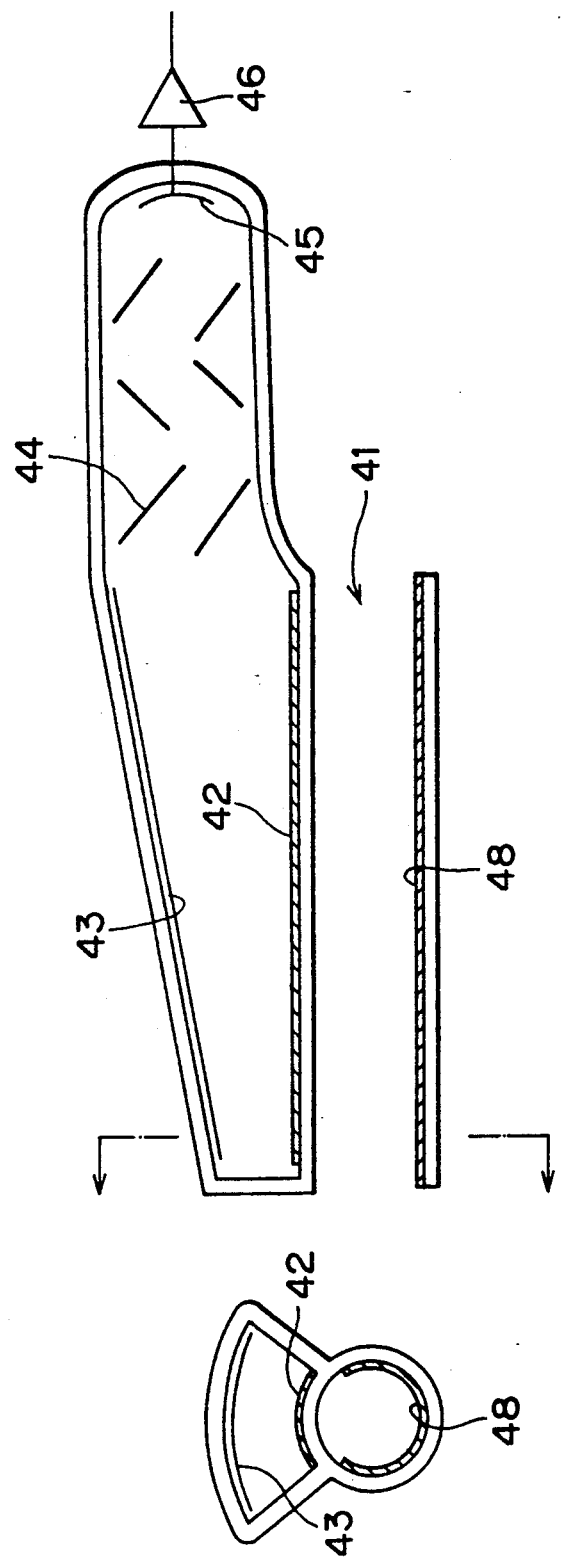
FIG. 6 is a cross-sectional view showing another example of a photodetector.

Furthermore, in lieu of the hollow photomultiplier 40, a photomultiplier of the type shown in FIG. 6 can be employed. The photomultiplier shown therein has a photocathode 42 on an inner arcuate surface of the photomultipler. A light reflective membrane 48 is provided partially in the inner circumference of the through-hole 41 in confronting relation to the photocathode 42. The photomultipler shown in FIG. 6 is advantageous in the simplicity of the internal arrangement. Semiconductor devices can also be employed as the photodetector.

As described, above according to the present invention, the fine particle advancing in the interior of the photomultiplier is kept irradiated by the exciting light. Therefore, a period of time during which the florescence is produced can be prolonged. Further, with the use of the hollow multiplier having a detecting surface formed in the entire inner circumference of a through-hole, fluorescence in any of the directions can be captured. Accordingly, fluorescence produced from successively supplied fine particles such as DNA bases can be detected with high accuracy and excellent efficiency.

What is claimed is:

1. A device for detecting fluorescence produced from a fine particle, comprising:

supplying means for supplying fine particles in a first direction;

blowing means for blowing the fine particles received from said supplying means in a second direction at a speed higher than a speed at which the fine particles are supplied from said supplying means;

irradiating means for irradiating an exciting light onto the fine particles blown by said blowing means, said irradiating means having an optical axis in alignment with the second direction in which the fine particles are blown by said blowing means; and detecting means for receiving the blown and irradiated fine particles and for detecting fluorescence produced from the fine particles which are excited by the exciting light of said irradiating means and which are blown by said blowing means.

2. The device according to claim 1, wherein the second direction in which the fine particles are blown by said blowing means is substantially orthogonal to the first direction in which the fine particles are supplied by said supplying means.

3. The device according to claim 1, wherein the second direction in which the fine particles are blown by said blowing means is substantially parallel to the first direction in which the fine particles are supplied by said supplying means.

4. The device according to claim 1, wherein said detecting means is a body formed with a through-hole through which the exciting light passes and through which the fine particles are blown by said blowing means.

5. The device according to claim 2, wherein said detecting means comprises a hollow photomultiplier formed with a through-hole defined by an inner circumference, said photomultiplier and having a photocathode deposited around said inner circumference of said through-hole for detecting the fluorescence produced from said fine particles, wherein a plurality of dynodes are located within the hollow photomultiplier for receiving the fluorescence detected by said photocathode, and an anode is located within the hollow photomultiplier for receiving the fluorescence detected by the photocathode and received by the plurality of dynodes, said photomultiplier being disposed so that the fine particles are blown by said blowing means through said through-hole.

6. The device according to claim 2, wherein said detecting means comprises a hollow photomultiplier which includes a through-hole, and wherein a reflective member is formed within said through-hole along an inner circumference thereof for reflecting the fluorescence produced from said fine particles, a photocathode is disposed within said hollow photomultiplier around said through-hole at a position opposite said reflective member to receive and detect the fluorescence reflected by said reflective member, a plurality of dynodes are located within the hollow photomultiplier for receiving the fluorescence detected by said photocathode, and an anode is located within the hollow photomultiplier for receiving the fluorescence detected by the photocathode and received by the plurality of dynodes, said photomultiplier being disposed so that the fine particles are blown by said blowing means through said through-hole.

7. The device according to claim 3, wherein said detecting means comprises a light receiving cylinder through which the fine particles are blown by said blowing means and a plurality of light detectors arranged circumferentially around said light receiving cylinder along the outside of the cylinder.

8. The device according to claim 7, wherein six light detectors are equi-angularly arranged circumferentially around said light receiving cylinder along the outside of the cylinder.

9. The device according to claim 7, wherein eight light-detectors are equi-angularly arranged circumferentially around said light receiving cylinder along the outside of the cylinder.

10. The device according to claim 1, wherein said supplying means supplies bases of DNA fragments.

* * * * *